United States Patent [19]

Suslov et al.

[11] Patent Number: 5,795,785
[45] Date of Patent: Aug. 18, 1998

[54] METHOD FOR THE DIAGNOSIS OF HUMAN MALIGNANT TUMORS

[76] Inventors: Eugene Ivanovich Suslov, 31$^B$ Polytechnicheskaya Str., Fl. 24, Kiev 252055; Konstantin Alexandrovich Galakhin, 89 Saksaganskiy Str., Fl. 21, Kiev 252032; Vitaly Alexandrovich Vladimirov, 35 Saksaganskiy Str., Fl. 39, Kiev 252033; Matveeevich Anatoly Novik, 06, Radyanskoy Ukzaine Str., Fl. 16, Kiev 252208, all of Ukraine

[21] Appl. No.: 454,208

[22] PCT Filed: Mar. 12, 1993

[86] PCT No.: PCT/UA93/00007

§ 371 Date: Aug. 7, 1995

§ 102(e) Date: Aug. 7, 1995

[87] PCT Pub. No.: WO94/14071

PCT Pub. Date: Jun. 23, 1994

[30] Foreign Application Priority Data

Dec. 10, 1992 [RU] Russian Federation ............. 93030251

[51] Int. Cl.$^6$ ............................................. G01N 33/574
[52] U.S. Cl. ............................. 436/64; 436/813; 435/7.23
[58] Field of Search ..................... 435/7.1, 7.23; 436/64, 813

[56] References Cited

PUBLICATIONS

Schomacker, K. et al. 1992 Nucl. Med. 31: 242–8.
Gibco—BRL. catalog. 1991. pp. 651, 653.
Lavenda, N 1985 Oncology 42(3): 201–204.
Underwood, JCE et al. 1988 J. Pathol. 155: 95–96.
Zvetkova, E. et al. 1979. Folia Haematol. 106(2): 205–223.
Dadoune, J.P. et al. 1991 Cell Tissue Res. 264:167–173.

*Primary Examiner*—Toni R. Scheiner
*Attorney, Agent, or Firm*—Ilya Zborovky

[57] ABSTRACT

A method for the diagnosis of human malignancy is implemented in the following way: a blood smear from a patient finger is layered with a complexon solution and standard blood serum with a subsequent addition of a developer of Calcium-protein complexes, then after some time a comparison is made between the color and structure of the stain and a similarly obtained reference blood smear from a healthy individual and in case of differences a malignant tumor is diagnosed in the host. According to the invention various optimal ratios of reagents are offered enabling more reliable results.

4 Claims, No Drawings

METHOD FOR THE DIAGNOSIS OF HUMAN MALIGNANT TUMORS

BACKGROUND OF THE INVENTION

The given invention relates to medicine or, more precisely, clinical oncology and, in particular, is associated with the means of diagnosis for human malignant tumors, which can find application in mass prophylactic screenings of population.

One of the main problems of clinical oncology lies in the diagnosis of malignant tumors in the initial stage of their development when the existing methods of treatment are most effective. The oncologic science currently disposes of a number of methods for screening diagnosis of malignant neoplasms enabling judgement on the presence or absence of tumor at the time of examination.

In part, prophylactic mammography has gained vast ground, which is carried 15 out with the aim of early diagnosis for malignant neoplasms of the mammary gland in female population (A. G.Holleb. Review of Breast Cancer Screening Guidelines. Cancer Supplement, 1992;69:1911–1912).

A method for cytologic screening of malignant cervical tumors is also known (Guzick D. S. Efficacy for screening for cervical cancer. A review. Am. J.Public Health, 1978;68:125–134.) However, the use of the majority of the known methods for screening diagnosis is directed at identification of tumors in one organ only and during examination other malignant neoplasms can be overlooked.

That is why until now there is a problem of creating a universal method for the diagnosis of malignant tumors meeting the requirements of screening techniques.

A number of researchers hold that the most promising methods in this respect are those based on identification of tumor markers in the host biologic liquids, such as blood, in particular.

Thus, a method for the diagnosis of human malignant tumors is known, which is based on isolation of protein fractions specific for malignant growth in the blood of an individual examined. (Korotkoruchko V. P. Cancer sedimentation reaction in the diagnosis of tumor disease.—Kiev. Naukova dumka.—1967.—80 p.) This protein fraction was isolated by maintaining blood serum in a solution of hydrochloric acid with subsequent sedimentation of protein with nitric acid and its further dissolution in distilled water. The sediment of blood serum proteins from cancer patients thus formed was not dissolved in contrast to that from healthy individuals.

The reaction result termed cancer sedimentation reaction (CSR) was determined by visual assessment of the protein sediment.

This well-known method is universal and enables identification of various forms and sites of malignant neoplasms. However, it does not possess sufficient specificity, since CSR is often positive in inflammatory and other non-tumor disease. Besides, this method is rather labour consuming (blood serum from the person examined requires preparation) and traumatic (blood for examination is withdrawn from the vein). Therefore, such a method will be of low efficacy for mass prophylactic screenings.

SUMMARY OF THE INVENTION

This invention is based on the task of developing a method for the diagnosis of human malignant tumors, which with the help of an original technique for isolation, in a blood smear from the patient finger predominantly, of certain protein fractions (Calcium-protein complexes) characteristic of malignant growth, would enable increased specificity and sensitivity of the method with a concurrent decrease in its laboriousness and traumatism, which allows, in the final analysis, to apply this method for mass prophylactic screenings for cancer.

The task so posed finds its solution in the fact that in the method for human malignant tumor diagnosis based on identification of blood protein fractions specific for malignant growth, in accordance with the invention, a smear of blood taken predominantly from patient finger is prepared in the process of analysis with consequential layering on top the solution of complexon, standard blood serum and then a developer of Calcium-protein complexes (CPC) and following light exposure, the colour and structure of the stain obtained are compared to those on the standard similarly made using a blood smear from a healthy individual and, if differences are found a malignant tumor is diagnosed.

DESCRIPTION OF PREFERRED EMBODIMENTS

The method being patented enables, based on the suggested processing of a blood smear, visualization of CPC whose identification, in the authors' view, is a more reliable and informative sign of malignant growth. In the authors' opinion, in the process of malignified cells life cycle split off from their DNA and are shed into blood (shedding effect) and then trapped by lymphocytes and under certain conditions of processing suggested in compliance with this invention can be found even in a peripheral blood smear.

Thus, according to the invention the method allows to perform investigations using a finger blood smear which practically precludes development of complications and significantly reduces laboriousness.

The above pathogenesis is characteristic of tumors from any sites and of various histogenesis. Taking into consideration the above said one can assert that the method being patented is universal, easy to perform, non-traumatic, sufficiently specific and, hence, can be used for mass prophylactic population examination aimed at cancer screening.

In accordance with one of the aspects of the invention it is advisable to choose the concentration for complexon solution in the range from 1% to 25%. It was found that at the concentration of complexon solution below 1% the duration of the reaction is significantly prolonged, while at the concentration over 25% the smear structure (the grain pattern) is less pronounced.

Besides, it is also preferable to use a solution of nitrogen acid silver at a concentration within the range from 0.1% to 0.5% as a developer of CPC.

The solution of nitrogen acid silver is the most potent developer. If its concentration is chosen below 0.1% the reaction duration is increased, the stain is insufficiently colored and the grain pattern is weakly expressed. Higher concentrations of the solution namely over 0.5% result in staining the grain outlines and make the reaction identification more difficult.

An important aspect of the reaction is the compliance with the quantitative ratio of the reagents. In accordance with one variant of the method implementation it is advisable to choose the ratio between the complexon solution and the developer equal to (15+3):1.

The choice of complexon solution lower than 1.5 at the given ratio results in an insufficient staining of the spot, while that above 3 produces complete staining of 30% of the image.

Finally, in accordance with another aspect of the invention, the time of exposure may be optimal. Thus, during light exposure over 4 hours the spot structure is stained, while exposure for less than 2 hours results in an insufficient processing and respective reduction in the result informativeness. The essence of the patented method will be more understandable from a detailed description of the optimal variant given below and individual examples of diagnosis made in compliance with this method.

The patented method lies in the following: a complexon solution, e.g. 0.2 ml of the 5% solution is placed on top of a blood smear from a patient finger and evenly layered over a slide. Then, after about 5–10 min. 0.1 ml of standard blood serum of any group is layered on the same site with subsequent addition of 0.3 ml of CPC reagent developer (preferably solution of nitrogen acid silver). As a rule a solution of ethyleneglycol-bis (beta-aminoethyl ether)-N,N-tetraacetate is used as complexon or a solution of di-sodium salt ethylenediamin-N,N,N,N-tetraacetate. AU the above reagents are added under light with subsequent exposure for 2–4 hours.

The result is recorded according to differences in color and structure of the stain obtained after the reaction on the patient and reference smears. The latter is a blood smear from a finger of a patient recognized as a healthy individual and is prepared similar to the patient smear. Numerous experiments with blood smears of healthy individuals enabled identification of features characteristic of the reference: yellow or yellow-brown coloring of the stain edge, light brown grains with distinct outlines in the middle and central zones of the stain.

If the color and structure of the stain in the smear coincide with the reference sample this points to the absence of malignancy in the host.

If the marginal zone of the blood smear stain is light brown or brown, while the middle and central zones show dark brown or hazel-brown grains with indistinct outlines the result testifies to the presence of malignancy.

Various cases of diagnosis in accordance with the method described are presented in the examples 1–8 below.

EXAMPLE 1

A blood smear from patient A. withdrawn from his finger during prophylactic examination was delivered. The patient had no complaints during examination. The smear was layered with 0.5 ml of the 15% EGTA solution. After 10 min. 0.1 ml of standard blood serum were added with subsequent application of 0.3 ml of nitrogen acid silver at 0.2%. The reagents were applied under light. The results were evaluated after 2.5 hr.

The smear from patient A. features a stain with a light brown marginal zone. The grains of the stain are dark brown with indistinct outlines. They converge in the middle and central zones forming a homogenous site with irregular outlines. The comparison of the pattern with the reference shows marked differences in grain coloring which testifies to the presence of malignancy. Clinico-roentgenologic and endoscopic examination revealed Stage II gastric cancer.

Histologic conclusion—glandular carcinoma.

EXAMPLE 2

A blood smear from patient N. was delivered with suspected lung cancer.

The smear was layered with 0.5 ml of 5% solution of EGTA. 0.2 ml of standard blood serum were added to the same site and after a while 0.3 ml of 0.2% solution of nitrogen acid silver. The reagents were applied under light. The results were evaluated after 2 hours.

The reaction zone of the smear revealed marginal yellow brown coloring and brown grains with distinct outlines in the middle of the stain. The comparison and color of the stain fully coincide with the reference sample, which testifies to the absence of neoplasia. The diagnosis was confirmed by morphologic investigation of the biopsic material. The samples showed tuberculoma-caseoma.

EXAMPLE 3

A blood smear from patient M. was delivered who addressed a physician with complaints of enlarged neck lymph nodes. The patient rejected punction biopsy point-blank. The smear was layered with 0.3 ml of 15% EDTA. After some time 0.1 ml of standard blood serum were added with a subsequent addition of 0.1 ml of 0.1% solution of nitrogen acid silver. The reagents were applied under light. The results were evaluated after 4 hr. The smear showed a stain with a light brown marginal zone. The grains were dark brown with indistinct outlines converging in the middle and central zones and forming a homogenous outline. The comparison of the pattern with the reference showed marked differences testifying to malignancy. Further morphologic investigation confirmed the result (lymphosarcoma).

EXAMPLE 4

A blood smear was delivered from a pediatric patient K. whose relatives addressed a local hospital and wanted him to be examined due to weight loss and general poor health.

The smear was layered with 0.2 ml of 20% solution of EDTA and 0.1 ml of standard blood serum with subsequent addition of 0.1 ml of 0.4% solution of nitrogen acid silver. The reagents were applied under light. The results were evaluated within 2 hours.

The smear demonstrated a stain with a light brown marginal zone. The grain pattern is dark brown converging in the middle and central zones forming a homogenous site with irregular outlines. The comparison of the picture obtained with the reference showed marked differences in color and grain pattern which testifies to the presence of malignancy. The child was hospitalized at an oncologic institution where following scrutinous examination he was diagnosed as having a right-sided Whilm's tumor. The morphologic examination of the removed sample revealed embryonal nephroblastoma.

EXAMPLE 5

A smear from patient C. was delivered withdrawn from finger during mammary gland surgery (sectoral resection).

The smear was layered with 0.25 ml of 10% solution of EGTA. 0.3 ml of standard blood serum were added and 0.1 ml of 0.2% solution of nitrogen acid silver. The reagents were applied under light. The results were evaluated within 3 hours.

The smear of patient C. showed a stain with a light brown marginal zone. The grain pattern of the stain was dark brown with indistinct outlines converging in the middle and central zones and forming a homogenous site with irregular outlines. The comparison of the picture with the reference shows marked differences in coloring and grain pattern which testifies to the presence of malignancy. The result coincided with histologic findings (adenocarcinoma).

EXAMPLE 6

A blood smear from patient C. was delivered with a suspicion of colonic malignant tumor.

The smear was layered with 0.2 ml of 25% solution of EGTA, to which 0.1 ml of standard blood serum were added and 0.1 ml of 0.5% solution of nitrogen acid silver. The reagents were applied under light. The results were evaluated after 2 hr.

The smear showed a stain with a light brown marginal zone. The grain pattern of the stain was dark brown with indistinct outlines converging in the middle and central zones forming a homogenous site with irregular outlines. The comparison of the picture with the reference shows marked differences in color and grain pattern which testifies to the presence of malignancy. Rectoromanoscopy revealed a tumor of the upper ampullary compartment of the rectum. Histologic conclusion—adenocarcinoma.

EXAMPLE 7

A blood smear from patient D. was delivered who addressed physicians because of a dark red neoplasm on the back skin.

The smear was layered with 0.15 ml of 3% solution of EDTA and 0.2 ml of standard blood serum with subsequent addition of 0.1 ml of 0.4% solution of nitrogen acid silver. The reagents were applied under light. The results were evaluated within 2 hr.

The smear of patient D. showed a stain with a light brown marginal zone. The stain grain pattern is dark brown with indistinct outlines converging in the middle and central zones forming a homogenous site with irregular outlines. The comparison of the picture with the reference shows marked differences in color and grain pattern which testifies to the presence of malignancy. The patient was subject to wide tumor dissection within boundaries of healthy tissues. Histologic conclusion—melanoma.

EXAMPLE 8

A blood smear from patient L. was delivered who addressed a gynecologist with complaints of bloody exudates from the vagina.

The smear was layered with 0.3 ml of 15% solution of EGTA, 0.3 ml of standard blood serum and 0.2 ml of 0.5% solution of nitrogen acid silver. The reagents were applied under light. The results were evaluated within 4 hours.

The smear of patient L. shows a stain with a light brown marginal zone. The grain pattern of the stain is dark brown with indistinct outlines converging in the middle and central zones and forming a homogenous site with irregular outlines. The comparison of the picture with the reference shows marked differences in color and grain pattern which testifies to the presence of malignancy. The patient was subjected to diagnostic scratching out. The histologic examination revealed planocellular cervical cancer.

The diagnostic effectiveness assessment of the method was performed in keeping with recommendations of the Committee of Experts of the International Federation for Clinical Chemistry in Reference Values.

In order to establish the diagnostic sensitivity and specificity we studied the results of the method application in 50 healthy individuals (donors) and patients with cancer of the esophagus, stomach, rectum, mammary gland, cervix and the lymphatic system (50 patients in each group).

Sensitivity and specificity were determined according to the generally accepted techniques. The results are presented in Tables 1 and 2.

TABLE 1

The results of cancer patients examination using the method in accordance with the invention.

| Tumor site | Number of patients | Number of true positive results abs. | Number of false positive results abs. | Diagnostic sensitivity % |
|---|---|---|---|---|
| Lungs | 50 | 44 | 6 | 88 |
| Esophagus | 50 | 43 | 7 | 86 |
| Stomach | 50 | 46 | 4 | 92 |
| Rectum | 50 | 45 | 5 | 90 |
| Mammary gland | 50 | 46 | 4 | 92 |
| Cervix | 50 | 46 | 4 | 92 |
| Lymphatic tissue | 50 | 43 | 7 | 86 |
| Total | 350 | 313 | 37 | 89.4 |

TABLE 2

The results of investigation of healthy individuals (donors) using a patented method.

| Examined individuals | Number of examined individuals abs. | Number of true negative results abs. | Number of positive results abs. | Diagnostic specificity % |
|---|---|---|---|---|
| Donors | 50 | 43 | 7 | 86 |

The method for the diagnosis of human malignant tumors is not traumatic, is highly informative and easy to perform.

This method can be used for the diagnosis of all malignant neoplasms. Its high diagnostic sensitivity (89.4%) and specificity (86%) allow to view its application as promising for screening of malignant tumors during mass prophylactic screenings of population.

We claim:

1. A method of diagnosing human malignant tumors based on identification of protein fractions specific for malignant growth, the method comprising the steps of:

preparing a test smear from blood withdrawn from a patient;

consecutively layering the test smear with a solution of complexon selected from the group consisting of EDTA and EGTA, standard blood serum and a developer of calcium-protein complexes which is a solution of nitrogen acid silver;

subjecting the layered serum to a light exposure to obtain a test stain;

comparing the test stain to a reference stain prepared in a similar manner on a blood smear from a healthy individual; and diagnosing malignancy if the margin of the test stain is brown or dark brown, rather than yellow-brown, in comparison with the margin of the reference stain, and if dark brown grains with indirect outlines are visible in the central zone of the test stain, in comparison with light brown grains with distinct outlines visible in the central zone of the reference stain.

2. The method as defined in claim 1, wherein the complexon solution concentration is equal to between 1% and 25%.

3. The method as defined in claim 1, wherein the ratio between the complexon solution and a solution of the developer is equal to (1.5–3):1.

4. A method as defined in claim 1, wherein said subjecting includes subjecting to a light exposure over a time between 2 and 4 hours.

* * * * *